United States Patent [19]

Harvey et al.

[11] 4,350,680
[45] Sep. 21, 1982

[54] DENTIFRICE

[75] Inventors: Kenneth Harvey, Wilmslow; Harry Hayes, Warrington; Anthony J. Morton, Withington, all of England

[73] Assignee: Colgate-Palmolive Company, New York, N.Y.

[21] Appl. No.: 304,438

[22] Filed: Sep. 21, 1981

[30] Foreign Application Priority Data

Sep. 24, 1980 [GB] United Kingdom ................ 8030772

[51] Int. Cl.³ .......................... A61K 7/16; A61K 7/18
[52] U.S. Cl. ........................................ 424/52; 424/49; 424/56; 424/57
[58] Field of Search ...................................... 424/49–58

[56] References Cited

U.S. PATENT DOCUMENTS

| 4,036,950 | 7/1977 | Baines et al. | 424/57 |
| 4,123,517 | 10/1978 | Baines et al. | 424/57 |
| 4,238,476 | 12/1980 | Harvey | 424/57 |
| 4,264,580 | 4/1981 | Barberio | 424/57 |
| 4,301,143 | 11/1981 | Barberio | 424/57 |

Primary Examiner—Shep K. Rose
Attorney, Agent, or Firm—Robert L. Stone; Murray M. Grill; Herbert S. Sylvester

[57] ABSTRACT

A dentifrice comprising an impure insoluble sodium metaphosphate polishing agent is disclosed, the dentifrice using a mixture of anionic phosphates esters as a surface active agent, to reduce or prevent a tendency to cause sloughing or desquamation.

11 Claims, No Drawings

DENTIFRICE

This invention relates to a dentifrice. In particular, it relates to a dental cream which reduces or avoids the incidence of sloughing or desquamation of oral mucosa.

There are numbers of people who have oral mucosa which are sufficiently sensitive so as to be removed by desquamation or sloughing during the normal toothbrushing regimen, e.g. twice a day for one to two minutes each time. Others may have desquamation occur with more rigorous brushing. This is essentially a cosmetic problem since the mucosa tends to form an unsightly residue at the teeth and lips. There is no pain and the mucosa cells are quickly regrown.

Dentifrices such as dental creams and tooth powders typically contain a dentally acceptable water-insoluble dental polishing agent. Insoluble sodium metaphosphate which has a water-soluble impurity content of about 2–4% is among the most commonly used dental polishing agents. Likewise, such dentifrices also generally also contain a water-soluble surface active agent, among which sodium lauryl sulphate is very common.

Unfortunately, when dentifrices contain both insoluble sodium metaphosphate including a soluble content and an anionic surface active agent such as sodium lauryl sulphate, sensitive users readily undergo oral sloughing, almost regardless of the pH of the dentifrice (e.g. about 3–7). Since the insoluble sodium metaphosphate is a highly desirable dental component, for instance in anticaries dental creams including a fluorine providing agent such as stannous fluoride or sodium monofluororphosphate, it became important to determine whether a surface active agent could be found which has the desirable anionic foaming and detersive characteristics of sodium lauryl sulphate but which reduces or avoids sloughing of oral mucosa when in contact with insoluble sodium metaphosphate having about 2–4% water-insoluble impurities.

According to the present invention a dentifrice comprises 20–99% by weight of a polishing agent of insoluble sodium metaphosphate having a water-soluble impurity content of 2–4% by weight and at least 0.2% by weight of an anionic phosphate ester surface active agent comprising a mixture of monoester of the formula

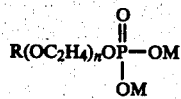

and diester of the formula

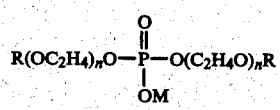

wherein R is an alkyl group of 10–20 carbon atoms, n a number from 1–6 and M is hydrogen, alkali metal or ammonium. These anionic phosphate ester surface active agents have been found to be surprisingly effective in reducing or preventing sloughing, while retaining advantages of anionic surface-active agents, such as foaming and detersiveness.

It is noted that anionic phosphate esters are disclosed as dentifrice surface active components in British Pat. No. 1,475,251 for oral preparations containing a cationic antibacterial agent. These preparations, when dental creams or tooth powders, preferably contain a nonionic polishing material. Alternatively, salts could be present but it was stated to be desirable that in the case of insoluble sodium metaphosphate that it be preferably substantially free of water-soluble content. In the present invention, insoluble sodium metaphosphate having a solubles content of about 2–4%, as is typical of commercial grades, is employed.

British Pat. No. 1,475,252 also discloses toothpastes containing the anionic phosphate esters. Insoluble sodium metaphosphate may be present but it is mixed with a substantial amount of alpha alumina trihydrate and is again preferably substantially free of water-solubles content. It is noteworthy that even sensitive dentifrice users would have little sloughing problem if alpha alumina trihydrate is present in substantial amount together with sodium lauryl sulphate.

It is an advantage of this invention that a substantially non-sloughing dentifrice containing insoluble sodium metaphosphate having a solubles content of about 2–4% is provided.

It is a further advantage of this invention that the non-sloughing dentifrice may contain an anticaries fluorine providing agent such as sodium monofluorophosphate or stannous fluoride.

Additional advantages will be apparent from consideration of the following specification.

The anionic phosphate esters used in the dentifrices of the invention are mixtures of mono and di-esters of the formulas hereinabove set forth. Suitable materials are available from MoDo Kemi Aktiebolaget, formerly Berol Aktiebolaget, of Sweden under the name Berol (Berol is a Trade Mark) and may include an anionic tri-ester moiety too, as well as some non-ionic portion. Berol 729 has alkyl chain lengths of 16–18 carbon atoms and contains series of 4 ethylene oxide units. Berol 729 is generally used in neutralised or partially neutralised form.

Further anionic phosphate ester materials which may be used in acid or neutralised forms are Berol 525 which contains alkyl groups of 10–18 carbon atoms and series of 5 ethylene oxide units and Berol 513 which contains alkyl groups of 16–18 carbon atoms. However, Berol 525 is also preferred in neutralised or partially neutralised form. Further Berol anionic phosphate esters are available as Berol 521, Berol 724, and Berol 733. The weight ratio of mono-ester to di-ester may vary, but is typically from 1:10 to 10:1.

When the acid forms of the anionic phosphate ester surface active agents are neutralised or partially neutralised, alkali metal, preferably sodium, or ammonium cations are present.

The surface active agent is typically employed in the dentifrice in amount of 0.2–5% by weight, preferably 0.5–3% and most preferably 1–2%.

The preferred grade of anionic phosphate ester is Berol 513.

The insoluble sodium metaphosphate used in the dentifrices of the invention is the insoluble sodium salt of a polymetaphosphoric acid. It is known in the art as having been often suggested as a dentifrice polishing agent. It may be formed in any suitable manner, for example as illustrated by Thorpe's Dictionary of Applied Chemistry, Vol. 9 (fourth edition), pages 510–511. The forms of commercially available insoluble sodium metaphosphate known as Madrell's salt and Kurrol's salt are examples of suitable materials. These metaphosphate salts exhibit some solubility in water, but are commonly referred to as insoluble sodium metaphosphates. There is present a minor amount of soluble phosphate material (e.g. sodium tripolyphosphate etc.) as impurities, usually of the order of several percent such as up to about 4% (e.g. 2-4%) by weight.

A minor amount (up to about half the total polishing material typically 1-10% by weight of the total) of an additional dentally acceptable polishing agent, particularly a water-insoluble calcium or magnesium salt, may be admixed with the insoluble sodium metaphosphate. Such agents include dicalcium orthophosphate dihydrate, anhydrous dicalcium orthophosphate, tricalcium phosphate, calcium pyrophosphate, magnesium orthophosphate and trimagnesium phosphate. The polishing material comprises 20-99% weight, typically 20-75% by weight of a dental cream and preferably 35-55%, and 75-99% by weight of a tooth powder.

It has also been found that an additional surface active agent may be present and desquamation further reduced, so long as the dental cream includes at least 0.2% by weight of the anionic phosphate ester. The additional surface active agent can even include sodium lauryl sulphate. Such additional agent may be anionic, nonionic, cationic or ampholytic in nature, and it is preferred to employ as the surface-active agent detersive material which imparts to the dentifrice detersive and foaming properties. Suitable types of such detergents are water-soluble salts of higher (i.e. having at least 12 carbon atoms) fatty acid monoglyceride monosulphates, such as the sodium salts of the nonsulphated monoglyceride of hydrogenated coconut oil fatty acids, higher alkyl sulphates, such as sodium lauryl sulphate, alkyl aryl sulphonates, such as sodium dodecyl benzene sulphonate, olefin sulphonates, such as sodium olefin sulphonate in which the olefin group contains 12-21 carbon atoms, higher alkyl sulphoacetates, higher fatty acid esters of 1,2 dihydroxy propane sulphonates, and the substantially saturated higher aliphatic acyl amides of lower (i.e. having not more than 4 carbon atoms) aliphatic amino carboxylic acid compounds, such as those having 12-16 carbons in the fatty acid, alkyl or acyl radicals. Examples of the last mentioned amides are N-lauroyl sarcosine, and the sodium, potassium and ethanolamine salts of N-lauroyl, N-myristoyl or N-palmitoyl sarcosine, which should be substantially free from soap or similar higher fatty acid material which tends to substantially reduce the effect of these compounds. The use of these sarcosine compounds in dentifrices is particularly advantageous since these materials exhibit a prolonged and marked effect in the inhibition of acid formation in the oral cavity due to carbohydrates breakdown in addition to exerting some reduction in the solubility of tooth enamel in acid solutions.

Other particularly suitable surface-active materials include nonionic agents such as condensates of sorbitan monostearate with approximately 60 moles of ethylene oxide condensates of ethylene oxide with propylene oxides condensates of propylene glycol ("Pluronics"— Pluronic is a Trade Mark) and amphoteric agents such as quaternised imidazole derivates, which are available under the trade mark "Miranol" such as Miranol C2M. It is noteworthy that nonionic and amphoteric agents assist in reducing sloughing. Quaternised imidazoles such as Miranol C2M are particularly preferred in this regard. Cationic surface active germicides and antibacterial compounds such as disobutylphenoxyethoxyethyl dimethyl benzyl, ammonium choloride, benzyl dimethyl stearyl ammonium chloride, tertiary amines having one fatty alkyl group (of from 12-18 carbon atoms) and two (poly)oxyethylene groups attached to the nitrogen (typically containing a total of from 20 to 50 ethanoxy groups per molecule) and salts thereof with acids, and compounds of the structure

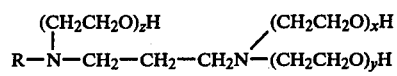

wherein R is a fatty alkyl group typically containing from 12 to 18 carbon atoms, and x, y and z total 3 or higher, as well as salts thereof with mineral or organic acids, may also be used.

In certain forms of this invention a fluorine-providing compound is present in the oral preparation. These compounds may be slightly soluble in water or may be fully water-soluble. They are characterised by their ability to release fluoride ions in water and by substantial freedom from reaction with other compounds of the oral preparation. Among these materials (including mixtures thereof) are inorganic fluoride salts, such as suitable alkali metal, alkaline earth metal, and heavy metal salts, for example, sodium fluoride, potassium fluoride, ammonium fluoride, a copper fluoride, such as cuprous fluoride, zinc fluoride, a tin fluoride such as stannous fluoride or stannous chlorofluoride, sodium fluorosilicate, ammonium fluorosilicate, sodium fluorosilicate, ammonium fluorosilicate, sodium fluorozirconate, sodium monofluorophosphate, aluminium mono and difluorophosphate, and fluorinated sodium calcium pyrophosphate. Alkali metal and tin fluorides such as sodium and stannous fluorides and particularly sodium monofluorophosphate are preferred.

The amount of the fluorine-providing compound is dependent to some extent upon the type of compound, its solubility, and the type of dentifrice, but it must be a non-toxic amount. It is considered that an amount of such compound which releases a maximum of 1% by weight, based on the weight of the dentifrice, is satisfactory. Any suitable minimum amount of such compound may be used, but it is preferable to employ sufficient compound to release from 0.005% to 1%, most preferably about 0.1% by weight of fluoride ion. Typically, in the cases of alkali metal fluoride and stannous fluoride, this component is present in an amount up to 2% by weight, based on the weight of the dentifrice and preferably in the range of from 0.05% to 1%. In the case of sodium monofluorophosphate the compound may be present in an amount up to 7.6% by weight, more typically 0.76%.

Various other materials may be incorporated in the oral preparations of this invention. Examples of colouring or whitening agents, preservatives, anti-oxidants, silicones, chlorophyll compounds, and ammoniated material such as urea, diammonium phosphate, and mixtures thereof. These adjuvants, where present, are incorporated in the preparations in amounts which do not substantially adversely affect the properties and characteristics desired.

Any suitable flavouring or sweetening materials may also be employed. Examples of suitable flavouring constituents are flavouring oils, e.g. oils of spearmint, peppermint, wintergreen, sassafras, clove, sage, eucalyptus, marjoram, cinnamon, lemon and orange, and methylsalicylate. Suitable sweetening agents include sucrose, lactose, maltose, sorbitol, sodium cyclamate, perillartine, and saccharin. Suitably, flavour and sweetening agent may together comprise from 0.01% to 5% or more of the preparation.

The dentifrice typically has a pH of 3-8, preferably 3-6. When reference is made to the pH herein, it is intended that the pH determination be made directly on the composition.

The dental creams are typically prepared by dispersing polishing material in the dental vehicle and adding the phosphate ester and other components thereto.

The following Examples are further illustrative of the present invention. All amounts are by weight unless otherwise indicated.

EXAMPLES

The dental creams are prepared having the following formulations:

| | PARTS | | | | | |
|---|---|---|---|---|---|---|
| | A | B | C | D | E | F |
| Sorbitol (70% solution) | 23.00 | 23.00 | 23.00 | 23.00 | 23.00 | 23.00 |
| Viscarin | 1.40 | 1.40 | 1.40 | 1.40 | 1.40 | 1.40 |
| Saccharin acid | 0.14 | 0.14 | 0.14 | 0.14 | 0.14 | 0.14 |
| Insoluble sodium metaphosphate (3.53% solubles) | 45.00 | 45.00 | 45.00 | 45.00 | 45.00 | 45.00 |
| Titanium dioxide | 0.40 | 0.40 | 0.40 | 0.40 | 0.40 | 0.40 |
| Ascorbic acid | 0.40 | 0.40 | 0.40 | 0.40 | 0.40 | 0.40 |
| Stannous fluoride | 0.62 | 0.62 | — | 0.62 | — | — |
| Sodium lauryl sulphate | 1.50 | 0.75 | 0.75 | 0.38 | 0.38 | — |
| Berol (513) (neutralised) | — | 0.75 | 0.75 | 1.12 | 1.12 | 0.75 |
| Quaternised imidazole (Miranol C2M) | — | — | — | — | — | 0.75 |
| Water | 26.54 | 26.54 | 21.16 | 26.54 | 27.16 | 26.54 |
| Flavour | 1.00 | 1.00 | 1.00 | 1.00 | 1.00 | 1.00 |

Panels of users rinse with 1:1 dental creams-water slurries of each dental cream A-F once per day on different days. The subjects using dental cream A have moderately heavy sloughing of oral mucosa while those using dental creams B-F have only slight to very slight sloughing. Retention of soluble tin and fluoride with dental creams B and D is quite good too.

We claim:

1. A dentifrice which reduces sloughing of oral mucosa in the oral cavity comprising 20-99% by weight of a polishing agent consisting essentially of an agent selected from the group consisting of insoluble sodium metaphosphate having a water-soluble impurity content of 2-4% by weight and a mixture of said insoluble sodium metaphosphate with up to half the total polishing agent of water-insoluble calcium or magnesium salt, and surface active agent which in combination with said insoluble sodium metaphosphate tends to cause oral sloughing, and additional anionic surface active agent in amount of at least 0.2% by weight of an anionic phosphate ester surface active agent comprising a mixture of monoester of the formula

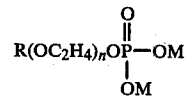

and diester of the formula

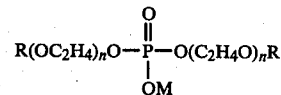

wherein R is an alkyl group of 10-20 carbon atoms, n a number from 1-6 and M is hydrogen, alkali metal or ammonium.

2. A dentifrice as claimed in claim 1 wherein the weight ratio of mono-ester to di-ester is from 1:10 to 10:1.

3. A dentifrice as claimed in claim 1 wherein R is an alkyl group of 16-18 carbon atoms.

4. A dentifrice as claimed in claim 1 wherein the anionic phosphate ester surface active agent is present in amount of 0.2-5% by weight.

5. A dentifrice as claimed in claim 1 wherein a fluorine-providing compound is present in amount to release up to about 1% by weight of fluoride.

6. A dentifrice as claimed in claim 5 wherein up to 2% by weight of stannous fluoride is present.

7. A dentifrice as claimed in claim 1 wherein a nonionic or amphoteric surface-active agent is also present.

8. A dentifrice as claimed in claim 7 wherein a quaternised imidazole amphoteric surface-active agent is present.

9. A dentifrice as claimed in claim 4 wherein surface active agent is present in amount of 0.5-3% by weight.

10. A dentifrice as claimed in claim 1 wherein said polishing agent consists essentially of said insoluble sodium metaphosphate.

11. A dentifrice as claimed in claim 1 wherein the surface active agent which tends to cause oral sloughing in combination with the insoluble sodium metaphosphate is sodium lauryl sulphate.

* * * * *